United States Patent [19]

Castro Pineiro et al.

[11] Patent Number: 6,025,374

[45] Date of Patent: Feb. 15, 2000

[54] AZETIDINE, PYRROLIDINE AND PIPERIDINE DERIVATIVES AS 5HT1 RECEPTOR AGONISTS

[75] Inventors: Jose Luis Castro Pineiro, Bishops Stortford; Caroline Henry, Norwich, both of United Kingdom; Victor Giulio Matassa, Rome, Italy; Austin John Reeve, Great Dunmow, United Kingdom; Francine Sternfeld, London, United Kingdom; Leslie Joseph Street, Harlow, United Kingdom

[73] Assignee: Merck Sharp & Dohme, Ltd., Hoddesdon, United Kingdom

[21] Appl. No.: 08/849,700

[22] PCT Filed: Nov. 27, 1995

[86] PCT No.: PCT/GB95/02759

§ 371 Date: Jul. 28, 1997

§ 102(e) Date: Jul. 28, 1997

[87] PCT Pub. No.: WO96/17842

PCT Pub. Date: Jun. 13, 1996

[30] Foreign Application Priority Data

Dec. 6, 1994 [GB] United Kingdom .................. 9424627
Mar. 23, 1995 [GB] United Kingdom .................. 9505871

[51] Int. Cl.[7] ................... A61K 31/445; C07D 209/02; C07D 401/00; C07D 263/58
[52] U.S. Cl. ................. 514/326; 514/331; 514/376; 514/415; 514/414; 546/208; 548/221; 548/468; 548/491
[58] Field of Search .................... 514/326, 331, 514/376, 415, 414; 546/208; 548/221, 468, 491

[56] References Cited

FOREIGN PATENT DOCUMENTS

| 0 313 397 A1 | 4/1989 | European Pat. Off. . |
| 2 083 463 | 3/1982 | United Kingdom . |
| WO 91/18897 | 12/1991 | WIPO . |
| WO 93/00333 | 1/1993 | WIPO . |
| WO 93/20073 | 10/1993 | WIPO . |
| WO 94/02477 | 2/1994 | WIPO . |

Primary Examiner—Johann Richter
Assistant Examiner—Joseph Murray
Attorney, Agent, or Firm—Philippe L. Durette; Melvin Winokur

[57] ABSTRACT

A class of substituted azetidine, pyrrolidine and piperidine derivatives are selective agonists of 5-HT$_1$-like receptors, being potent agonists of the human 5-HT$_{1D\alpha}$ receptor subtype whilst possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, whilst eliciting fewer side-effects, notably adverse cardiovascular events, than those associated with non-subtype-selective 5-HT$_{1D}$ receptor agonists.

12 Claims, No Drawings

AZETIDINE, PYRROLIDINE AND PIPERIDINE DERIVATIVES AS 5HT1 RECEPTOR AGONISTS

The present invention relates to a class of substituted azetidine, pyrrolidine and piperidine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of heteroaromatic compounds based on inter alia a substituted tryptamine ring system are described in published International patent applications 91/18897, 94/02460 and 94/02477. The compounds described therein are stated to be agonists of 5-HT$_1$-like receptors, and accordingly to be of particular use in the treatment of migraine and associated conditions. None of these publications, however, discloses or even suggests the substituted azetidine, pyrrolidine and piperidine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the precisely substituted piperazine moiety described therein with a substituted azetidine, pyrrolidine or piperidine moiety.

Moreover, nowhere in the prior art available to date is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype.

The present invention provides a compound of formula I, or a salt or prodrug thereof:

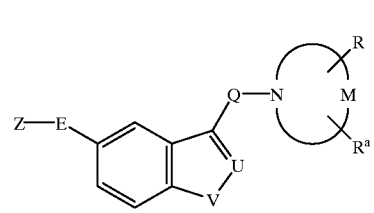

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (a), (b), (c) or (d):

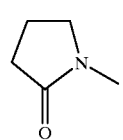

(a)

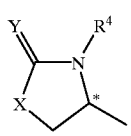

(b)

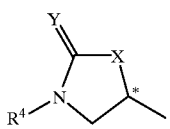
(c)

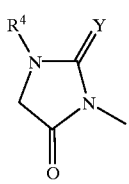
(d)

in which the asterisk * denotes a chiral centre;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 4 carbon atoms, optionally substituted in any position by a hydroxy group;

U represents nitrogen or C—$R^2$;

V represents oxygen, sulphur or N—$R^3$;

$R^2$, $R^3$ and $R^4$ independently represent hydrogen or $C_{1-6}$ alkyl;

$R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring;

M represents the residue of an azetidine, pyrrolidine or piperidine ring;

R represents a group of formula —W—$R^1$;

W represents a chemical bond or a straight or branched alkylene chain containing from 1 to 4 carbon atoms;

$R^1$ represents —$OR^x$, —$SR^x$ or —$NR^xR^y$;

$R^x$ and $R^y$ independently represent hydrogen, hydrocarbon or a heterocyclic group, or $R^x$ and $R^y$ together represent a $C_{2-6}$ alkylene group; and $R^a$ represents hydrogen, hydroxy, hydrocarbon or a heterocyclic group.

The present invention also provides compounds of formula I above, and salts and prodrugs thereof, wherein $R^5$ and $R^6$ independently represent hydrogen, $C_{1-6}$ alkyl, trifluoromethyl, methylphenyl, or an optionally substituted aryl($C_{1-6}$)alkyl or heteroaryl($C_{1-6}$)alkyl group.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$) alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups include phenyl and naphthyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The hydrocarbon and heterocyclic groups, as well as the aryl($C_{1-6}$)alkyl or heteroaryl($C_{1-6}$)alkyl groups $R^5$ and/or $R^6$, may in turn be optionally substituted by one or more groups selected from $C_{1-6}$ alkyl, adamantyl, phenyl, halogen, $C_{1-6}$ haloalkyl, $C_{1-3}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. For example, the compounds of formula I above wherein Z represents a group of formula (b) or (c) have a chiral centre denoted by the asterisk *, which may accordingly be in the (R) or (S) configuration. Where the compounds according to the invention possess two or more asymmetric centres, they may additionally exist as diastereoisomers. It is to be understood that all such isomers and mixtures thereof in any proportion are encompassed within the scope of the present invention.

In particular, where M represents the residue of a pyrrolidine ring, and the substituent R is attached to the 2-position thereof, then the absolute stereochemical configuration of the carbon atom at the point of attachment of the moiety R is preferably as depicted in structure IA as follows:

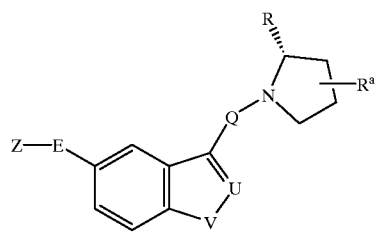

(IA)

wherein Z, E, Q, U, V, R and $R^a$ are as defined above.

Moreover, where M represents the residue of a pyrrolidine ring, and the substituent R is attached to the 3-position thereof, then the absolute stereochemical configuration of the carbon atom at the point of attachment of the moiety R is preferably as depicted in structure IB as follows:

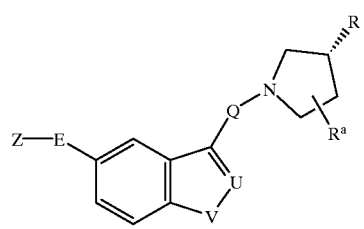

(IB)

wherein Z, E, Q, U, V, R and $R^a$ are as defined above.

Where E, Q and W, which may be the same or different, represent straight or branched alkylene chains, these may be, for example, methylene, ethylene, 1-methylethylene, propylene, 2-methylpropylene or butylene. In addition, the alkylene chain Q may be substituted in any position by a hydroxy group giving rise, for example, to a 2-hydroxypropylene or 2-hydroxymethyl-propylene chain Q. Moreover, E and W may each independently represent a chemical bond. Where E represents a chemical bond, the moiety Z is attached directly to the benzo moiety of the central fused bicyclic heteroaromatic ring system. Similarly, where W represents a chemical bond, the substituent $R^1$ is attached directly to the azetidine, pyrrolidine or piperidine ring of which M is the residue.

Suitably, E represents a chemical bond or a methylene linkage.

Suitably, Q represents an ethylene or propylene linkage.

The compound of formula I in accordance with the present invention is suitably an indole, benzofuran or benzthiophene derivative of formula IC, or an indazole derivative of formula ID:

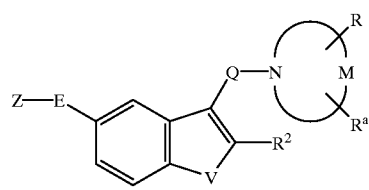

(IC)

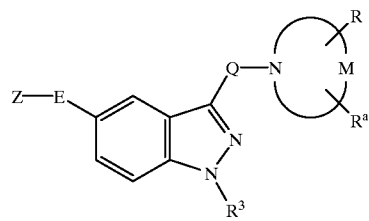

(ID)

wherein Z, E, Q, V, M, R, $R^a$, $R^2$ and $R^3$ are as defined above. Preferably, the compounds according to the invention are indole derivatives of formula IE:

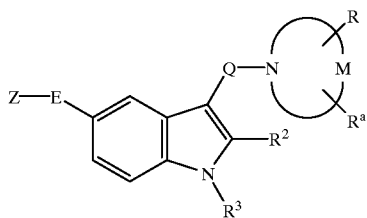

wherein Z, E, Q, M, R, $R^a$, $R^2$ and $R^3$ are as defined above, in particular wherein $R^2$ and $R^3$ are both hydrogen.

Suitably, W represents a chemical bond or a methylene linkage.

Suitably, $R^x$ and $R^y$ independently represent hydrogen, $C_{1-6}$ alkyl, aryl, aryl($C_{1-6}$)alkyl, heteroaryl or heteroaryl ($C_{1-6}$)alkyl, any of which groups may be optionally substituted by one or more substituents selected typically from halogen, hydroxy, $C_{1-6}$ alkoxy, amino, $C_{2-6}$ alkylcarbonylamino, $C_{1-6}$ alkylsulphonylamino and $C_{1-6}$ alkylaminosulphonylmethyl. Particular values of $R^x$ and $R^y$ include hydrogen, methyl, benzyl, fluorobenzyl, methoxybenzyl, acetylaminobenzyl, 1-phenylethyl, 2-phenylethyl, 2-hydroxy-1-phenylethyl, 1-(acetylamino-phenyl)ethyl, 2-(acetylamino-phenyl)ethyl, 1-hydroxy-3-phenylprop-2-yl, 1-hydroxy-1-phenylprop-2-yl, furylmethyl, thienylmethyl and pyridylmethyl.

Suitable values for the substituent $R^1$ include hydroxy, benzyloxy, methoxy-benzyloxy, pyridylmethoxy, amino, methylamino, benzylamino, N-(acetylamino-benzyl)-amino, N-(1-phenylethyl)-amino, N-(2-phenylethyl)-amino, N-(2-hydroxy-1-phenylethyl)-amino, N-[1-(acetylamino-phenyl)ethyl]-amino, N-[2-(acetylamino-phenyl)ethyl]-amino, N-(1-hydroxy-3-phenylprop-2-yl)-amino, N-(1-hydroxy-1-phenylprop-2-yl)-amino, N-(furylmethyl)-amino, N-(pyridylmethyl)-amino, dimethylamino, N-benzyl-N-methylamino, N-fluorobenzyl-N-methylamino, N-(acetylamino-benzyl)-N-methylamino, N-methyl-N-(1-phenylethyl)-amino, N-(2-hydroxy-1-phenylethyl)-N-methylamino, N-[2-(acetylamino-phenyl)ethyl]-N-methylamino and N-methyl-N-(thienylmethyl)-amino.

Particular values of the group R include hydroxy, benzyloxy, benzyloxymethyl, methoxy-benzyloxy, pyridylmethoxy, benzylamino, benzylaminomethyl, N-(acetylamino-benzyl)-amino, N-(acetylamino-benzyl)-aminomethyl, N-(1-phenylethyl)-amino, N-(1-phenylethyl)-aminomethyl, N-(2-hydroxy-1-phenylethyl)-amino, N-(2-hydroxy-1-phenylethyl)-aminomethyl, N-[1-(acetylamino-phenyl)ethyl]-amino, N-[1-(acetylamino-phenyl)ethyl]-aminomethyl, N-[2-(acetylamino-phenyl)ethyl]-amino, N-(1-hydroxy-3-phenylprop-2-yl)-amino, N-(1-hydroxy-1-phenylprop-2-yl)-amino, N-(furylmethyl)-aminomethyl, N-(pyridylmethyl)-aminomethyl, N-benzyl-N-methylamino, N-benzyl-N-methyl-aminomethyl, N-fluorobenzyl-N-methyl-aminomethyl, N-(acetylaminobenzyl)-N-methyl-aminomethyl, N-methyl-N-(1-phenylethyl)-aminomethyl, N-(2-hydroxy-1-phenylethyl)-N-methylamino, N-[2-(acetylamino-phenyl)ethyl]-N-methylamino and N-methyl-N-(thienylmethyl)amino.

Suitable values of $R^a$ include hydrogen, hydroxy and benzyl, especially hydrogen.

Suitably, $R^2$ and $R^3$ independently represent hydrogen or methyl, especially hydrogen.

Suitably, $R^4$ represents hydrogen or methyl.

Suitably, $R^5$ and $R^6$ are independently selected from hydrogen, methyl, ethyl, n-propyl, isopropyl, n-butyl, t-butyl, trifluoromethyl, phenyl, methylphenyl (especially 4-methylphenyl), benzyl and phenethyl.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, phenylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (a), (b), (c) or (d) as defined above.

In a particular embodiment, Z represents $-SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (b) in which $R^4$ is hydrogen or methyl. In a subset of this embodiment, X and Y both represent oxygen. In a particular aspect of this subset, the chiral centre denoted by the asterisk * is in the (S) configuration.

A particular sub-class of compounds according to the invention is represented by the compounds of formula IIA, and salts and prodrugs thereof:

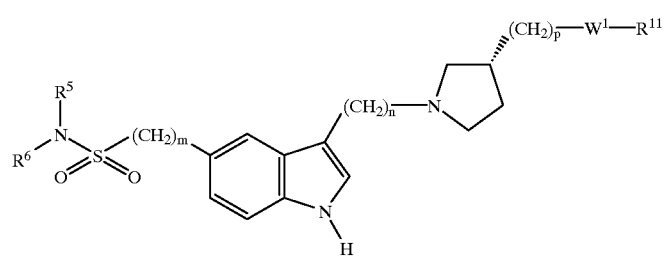

wherein m is zero, 1, 2 or 3, preferably zero or 1;

n is 2, 3 or 4, preferably 2 or 3;

p is zero, 1 or 2;

$R^5$ and $R^6$ are as defined with reference to formula I above;

$W^1$ represents oxygen, sulphur or N—$R^{12}$; and

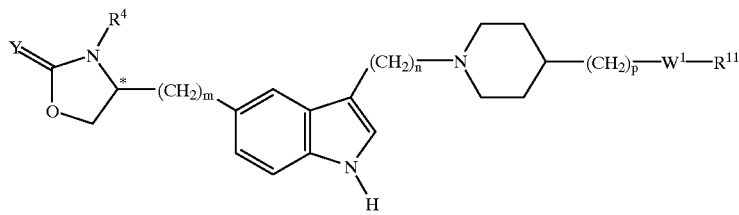

(IIC)

$R^{11}$ and $R^{12}$ independently represent hydrogen, $C_{1-6}$ alkyl, aryl, aryl($C_{1-6}$)alkyl, heteroaryl or heteroaryl ($C_{1-6}$)alkyl, any of which groups may be optionally substituted.

Examples of suitable optional substituents on the groups $R^{11}$ and $R^{12}$ include halogen, cyano, trifluoromethyl, hydroxy, $C_{1-6}$ alkoxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

Particular values of $R^5$ and $R^6$ with reference to formula IIA above include hydrogen and $C_{1-6}$ alkyl, especially hydrogen or methyl. Suitably, one of $R^5$ and $R^6$ represents hydrogen and the other represents hydrogen or methyl.

Particular values of $R^{11}$ and $R^{12}$ include hydrogen, methyl, benzyl, fluorobenzyl, methoxy-benzyl, acetylamino-benzyl, 1-phenylethyl, 2-phenylethyl, 2-hydroxy-1-phenylethyl, 1-(acetylamino-phenyl)ethyl, 2-(acetylamino-phenyl)ethyl, 1-hydroxy-3-phenylprop-2-yl, 1-hydroxy-1-phenylprop-2-yl, furylmethyl, thienylmethyl and pyridylmethyl.

Typically, $R^{11}$ represents benzyl, fluorobenzyl, 1-phenylethyl or 2-hydroxy-1-phenylethyl.

Typically, $R^{12}$ is hydrogen or methyl.

Another sub-class of compounds according to the invention is represented by the compounds of formula IIB, and salts and prodrugs thereof:

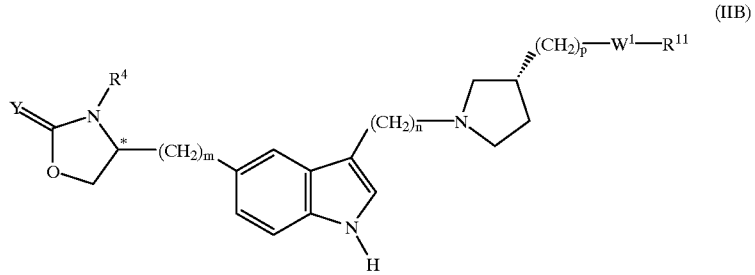

(IIB)

wherein the asterisk * denotes a chiral centre;

$R^4$ and Y are as defined with reference to formula I above; and m, n, p, $W^1$ and $R^{11}$ are as defined with reference to formula IIA above.

A further sub-class of compounds according to the invention is represented by the compounds of formula IIC, and salts and prodrugs thereof:

wherein the asterisk * denotes a chiral centre;

$R^4$ and Y are as defined with reference to formula I above; and m, n, p, $W^1$ and $R^{11}$ are as defined with reference to formula IIA above.

In relation to formula IIB and IIC above, the chiral centre denoted by the asterisk * is suitably in the (S) configuration.

Specific compounds within the scope of the present invention include:

(3S)-3-(N-benzyl)aminomethyl-1-[2-(5-(N-methyl)-aminosulphonylmethyl)-1H-indol-3-yl)ethyl]pyrrolidine;

(3S)-3-(N-benzyl)aminomethyl-1-[2-(5-(aminosulphonylmethyl)-1H-indol-3-yl)ethyl]pyrrolidine;

(3S)-3-(N-benzyl)aminomethyl-(S)-1-[2-(5-(2-oxo-1,3-oxazolidin-4-ylmethyl)-1H-indol-3-yl)ethyl]pyrrolidine;

(3S)-3-[N-(R)-α-(hydroxymethyl)benzyl]aminomethyl-(S)-1-[2-(5-(2-oxo-1,3-oxazolidin-4-ylmethyl)-1H-indol-3-yl)ethyl]pyrrolidine;

(3S)-3-[N-(S)-α-methylbenzyl]aminomethyl-(S)-1-[2-(5-(2-oxo-1,3-oxazolidin-4-ylmethyl)-1H-indol-3-yl)ethyl] pyrrolidine;

4-[N-(R)-α-(hydroxymethyl)benzyl]amino-(S)-1-[3-(5-(2-oxo-1,3-oxazolidin-4-ylmethyl)-1H-indol-3-yl)propyl] piperidine;

(3S)-3-(N-benzyl-N-methyl)aminomethyl-(S)-1-[2-(5-(3-methyl-2-oxo-1,3-oxazolidin-4-ylmethyl)-1H-indol-3-yl) ethyl]pyrrolidine;

(3R)-3-[N-(S)-α-methylbenzyl-N-methyl]aminomethyl-(S)-1-[2-(5-(2-oxo-1,3-oxazolidin-4-ylmethyl)-1H-indol-3-yl)ethyl]pyrrolidine;

(3R)-3-[N-(S)-α-methylbenzyl-N-methyl]aminomethyl-(S)-1-[2-(5-(3-methyl-2-oxo-1,3-oxazolidin-4-ylmethyl)-1H-indol-3-yl)ethyl]pyrrolidine;

(3S)-3-[N-(4-fluorobenzyl)-N-methyl]aminomethyl-(S)-1-[2-(5-(3-methyl-2-oxo-1,3-oxazolidin-4-ylmethyl)-1H-indol-3-yl)ethyl]pyrrolidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein U represents C—$R^2$ and V represents N—$R^3$, corresponding to the indole derivatives of formula IE as defined above, may be prepared by a process which comprises reacting a compound of formula III:

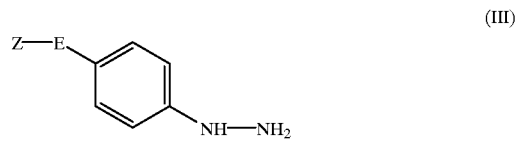

(III)

wherein Z and E are as defined above; with a compound of formula IV, or a carbonyl-protected form thereof.

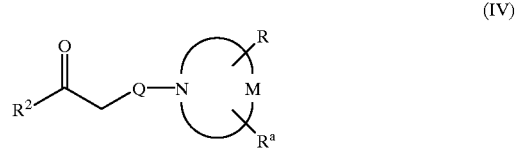

(IV)

wherein $R^2$, Q, M, R and $R^a$ are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives.

The Fischer reaction between compounds III and IV may be carried out in a single step, or may proceed via an initial non-cyclising step at a lower temperature to give an intermediate of formula V:

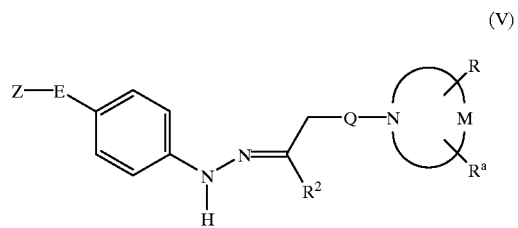

(V)

wherein Z, E, Q, $R^2$, M, R and $R^a$ are as defined above; followed by cyclisation using a suitable reagent, e.g. a polyphosphate ester.

The intermediates of formula IV, or carbonyl-protected forms thereof, may be prepared by reacting a compound of formula VI, or a carbonyl-protected form thereof, with a compound of formula VII:

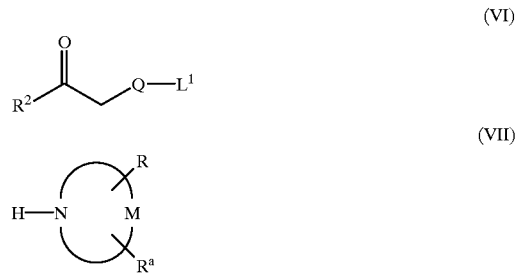

(VI)

(VII)

wherein Q, $R^2$, M, R and $R^a$ are as defined above, and $L^1$ represents a suitable leaving group.

The leaving group $L^1$ is suitably a halogen atom, e.g. chlorine or bromine.

Where L¹ represents a halogen atom, the reaction between compounds VI and VII is conveniently effected by stirring the reactants under basic conditions in a suitable solvent, for example sodium carbonate or potassium carbonate in 1,2-dimethoxyethane or N,N-dimethylformamide, or triethylamine in tetrahydrofuran or acetonitrile, optionally in the presence of catalytic sodium iodide.

In an alternative procedure, the compounds according to the invention may be prepared by a process which comprises reacting a compound of formula VII as defined above with a compound of formula VIII:

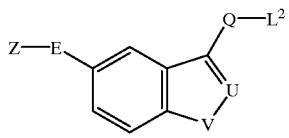

(VIII)

wherein Z, E, Q, U and V are as defined above, and L² represents a suitable leaving group.

The leaving group L² is suitably an alkylsulphonyloxy or arylsulphonyloxy group, e.g. methanesulphonyloxy (mesyloxy) or p-toluenesulphonyloxy (tosyloxy).

Where L² represents an alkylsulphonyloxy or arylsulphonyloxy group, the reaction between compounds VII and VIII is conveniently carried out in a suitable solvent such as isopropanol/acetonitrile N,N-dimethylformamide or 1,2-dimethoxyethane, typically in the presence of a base such as sodium carbonate or potassium carbonate, optionally in the presence of catalytic sodium iodide.

In one representative approach, the compounds of formula VIII wherein U represents CH, V represents NH and L² represents a mesyloxy or tosyloxy group may be prepared by the sequence of steps illustrated in the following reaction scheme (cf. Larock and Yum, *J. Am. Chem. Soc.*, 1991, 113, 6689):

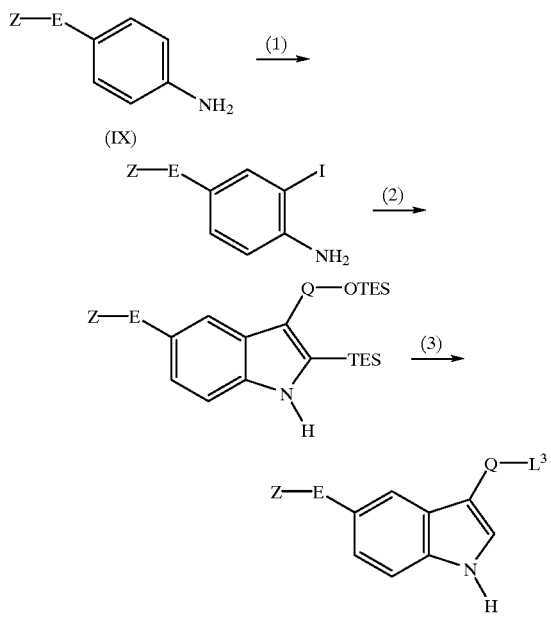

wherein Z, E and Q are as defined above, L³ represents mesyloxy or tosyloxy, and TES is an abbreviation for triethylsilyl.

In Step 1 of the reaction scheme, the aniline derivative IX is treated with iodine monochloride, typically in acetonitrile, in order to introduce an iodine atom ortho to the amine moiety. Step 2 involves a palladium-mediated coupling reaction with the protected acetylene derivative TES—C≡C—Q—OTES, typically using palladium acetate and triphenylphosphine in the presence of lithium chloride and sodium carbonate, suitably in N,N-dimethylformamide at an elevated temperature. This is followed in Step 3 by removal of the TES moiety, ideally in refluxing methanolic hydrochloric acid: followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula VIII wherein U represents CH, V represents NH, Q represents a propylene chain and L² represents a mesyloxy or tosyloxy group may be prepared by reacting 3,4-dihydro-2H-pyran with a compound of formula III as defined above or a salt thereof, under a variant of the Fischer reaction conditions as described above for the reaction between compounds III and IV; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating an acid addition salt of the hydrazine derivative III, typically the hydrochloride salt, in an inert solvent such as dioxan, at the reflux temperature of the solvent.

In a further procedure, the compounds according to the invention wherein U represents nitrogen and V represents N—R³, corresponding to the indazole derivatives of formula ID as defined above, may be prepared by a process which comprises cyclising a compound of formula X:

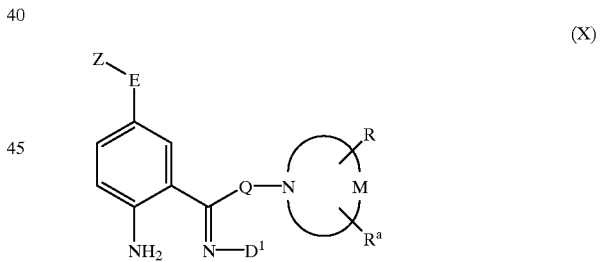

(X)

wherein Z, E, Q, M, R and Rᵃ are as defined above, and D¹ represents a readily displaceable group; followed, where required, by N-alkylation by standard methods to introduce the moiety R³.

The cyclisation of compound X is conveniently achieved in a suitable organic solvent at an elevated temperature, for example in a mixture of m-xylene and 2,6-lutidine at a temperature in the region of 140° C.

The readily displaceable group D¹ in the compounds of formula X suitably represents a $C_{1-4}$ alkanoyloxy group, preferably acetoxy. Where D¹ represents acetoxy, the desired compound of formula X may be conveniently prepared by treating a carbonyl compound of formula XI:

(XI)

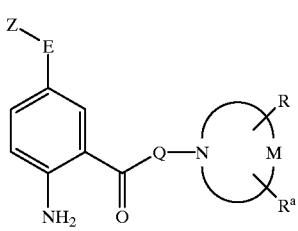

wherein Z, E, Q, M, R and $R^a$ are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

(XII)

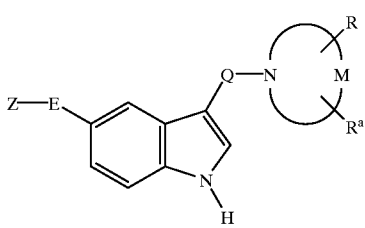

wherein Z, E, Q, M, R and $R^a$ are as defined above; followed by a reductive work-up, advantageously using dimethylsulphide.

The indole derivatives of formula XII may be prepared by methods analogous to those described in the accompanying Examples, or by procedures well known from the art.

In a still further procedure, the compounds according to the invention wherein U represents C—$R^2$ and V represents oxygen or sulphur, corresponding to the benzofuran or benzthiophene derivatives of formula IC wherein V is oxygen or sulphur respectively, may be prepared by a process which comprises cyclising a compound of formula XIII:

(XIII)

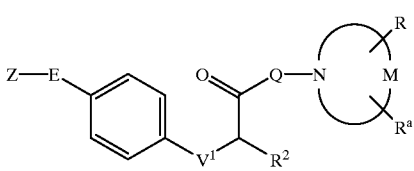

wherein Z, E, Q, $R^2$, M, R and $R^a$ are as defined above, and $V^1$ represents oxygen or sulphur.

The cyclisation of compound XIII is conveniently effected by using polyphosphoric acid or a polyphosphate ester, advantageously at an elevated temperature.

The compounds of formula XIII may be prepared by reacting a compound of formula XIV with a compound of formula XV:

(XIV)

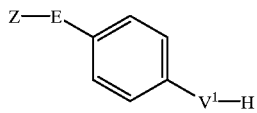

(XV)

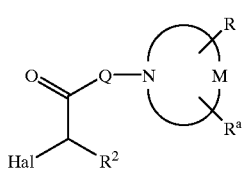

wherein Z, E, Q, $R^2$, $V^1$, M, R and $R^a$ are as defined above, and Hal represents a halogen atom.

The reaction is conveniently effected in the presence of a base such as sodium hydroxide.

The hydroxy and mercapto derivatives of formula XIV may be prepared by a variety of methods which will be readily apparent to those skilled in the art.

The hydrazine derivatives of formula III above may be prepared by methods analogous to those described in EP-A-0548813 and WO-A-91/18897, as also may the aniline derivatives of formula IX.

Where they are not commercially available, the starting materials of formula VI, VII and XV may be prepared by the methods described in the accompanying Examples, or by analogous procedures which will be apparent to those skilled in the art.

It will be understood that any compound of formula I initially obtained from any of the above processes may, where appropriate, subsequently be elaborated into a further compound of formula I by techniques known from the art. For example, a compound of formula I wherein $R^x$ is benzyl initially obtained may be converted into a compound of formula I wherein $R^x$ is hydrogen typically by conventional catalytic hydrogenation, or by transfer hydrogenation using a hydrogenation catalyst such as palladium on charcoal in the presence of a hydrogen donor such as ammonium formate. Moreover, a compound of formula I wherein $R^1$ is hydroxy initially obtained may be converted into the corresponding carbonyl compound (aldehyde or ketone) by treatment with a conventional oxidising agent such as sulphur trioxide-pyridine complex; the resulting carbonyl compound may then be converted in turn into a compound of formula I wherein $R^1$ represents —$NHR^y$, suitably by a standard reductive amination procedure which comprises treating the carbonyl compound with the appropriate amine of formula $R^y$—$NH_2$ in the presence of a suitable reducing agent, typically sodium cyanoborohydride. Similarly, a compound of formula I wherein $R^1$ represents —$NHR^y$ initially obtained may be converted into a further compound of formula I wherein $R^1$ represents —$NR^xR^y$, in which $R^x$ corresponds to the group —$CH_2R^z$, suitably by a reductive amination procedure which comprises treating the compound of formula I wherein $R^1$ represents —$NHR^y$ with the appropriate aldehyde of formula $R^z$—CHO in the presence of a reducing agent such as sodium cyanoborohydride. In addition, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organtic Synthesis*. John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D\alpha}$ receptor subtype, inhibit forskolin-stimulated adenylyl cyclase activity, and stimulate [$^{35}$S]-GTPγS binding to membranes from clonal cell lines expressing human cloned receptors.

$5\text{-HT}_{1D\alpha}/5\text{-HT}_{1D\beta}$ Radioligand Binding

Chinese hamster ovary (CHO) clonal cell lines expressing the human $5\text{-HT}_{1D\alpha}$ and $5\text{-H}_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [3H]-5-HT for saturation studies or 2–5 nM [3H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the $5\text{-HT}_{1D\alpha}$ receptor subtype obtained for the compounds of the accompanying Examples were below 50 nM in each case. Furthermore, the compounds of the accompanying Examples were all found to possess a selective affinity for the $5\text{-HT}_{1D\alpha}$ receptor subtype of at least 10-fold relative to the $5\text{-HT}_{1D\beta}$ subtype.

$5\text{-HT}_{1D\alpha}/5\text{-HT}_{1D\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D\alpha}$ and $5\text{-HT}_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541) Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the $5\text{-HT}_{1D\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D\alpha}$ receptor subtype relative to the $5\text{-HT}_{1D\beta}$ subtype.

$5\text{-HT}_{1D\alpha}/5\text{-HT}_{1D\beta}$ GTPγS Binding

Studies were performed essentially as described in *Br. J. Pharmacol.*, 1993, 109, 1120. CHO clonal cell lines expressing the human cloned $5\text{-HT}_{1D\alpha}$ and $5\text{-HT}_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the $5\text{-HT}_{1D\alpha}$ receptor transfected cells and 40–50 μg protein/ml for the $5\text{-HT}_{1D\beta}$ receptor transfected cells. The membrane suspension was then incubated. in a volume of 1 ml, with GDP (100 μM for $5\text{-HT}_{1D\alpha}$ receptor transfected cells, 30 μM for the $5\text{-HT}_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

EXAMPLE 1

(3S)-3-(N-Benzyl)aminomethyl-1-[2-(5-(N-(methyl) amino-sulphonylmethyl)-1H-indol-3-yl)ethyl] pyrrolidine 2.1 Hydrogen Oxalate 0.7 Diethyl Etherate 1. Intermediate 1: (3S)-N(H)-3-(N-Benzyl)aminomethyl-pyrrolidine a) (3R)-N-tert-Butyloxycarbonyl-3-hydroxymethylpyrrolidine A mixture of (3R)-N-[(R)-1-phenylethyl]-3-(hydroxymethyl)pyrrolidine (*J. Med. Chem.,* 1990, 33(1), 71; 17.0 g, 82.8 mmol), di-tert-butyldicarbonate (21.7 g, 99.4 mmol), Pearlman's catalyst (4.28 g, 25% w/w), methanol (300 ml) and water (40 ml) was hydrogenated on a Parr shake apparatus, at 40 psi, for 2.25 h. The mixture was filtered through a pad of celite and the pad washed with ethanol. The combined filtrate and washings were evaporated and the residue chromatographed on silica gel eluting with $CH_2Cl_2$/MeOH (95:5) to give the title-pyrrolidine (16.73 g, 100%), δ (250 MHz, $D_6$-DMSO) 1.39 (9H, s, OC(Me)$_3$), 1.31–1.64 (2H, m, $CH_2$), 1.79–1.88 (1H, m, CH), 2.19–2.31 (1H, m, CH of $CH_2$), 2.95 (1H, dd, J=10.7 and 7.0Hz, CH of $CH_2$), 3.11–3.35 (4H, m, 2 of $CH_2$), 4.67 (1H, t, J=5.3Hz, OH).

b) (3R)-N-tert-Butyloxycarbonyl-3-methylsulphonyl-oxymethylpyrrolidine

A solution of methane sulphonyl chloride (3.37 g, 29.39 mmol) in $CH_2Cl_2$ (30 ml) was added dropwise to a solution of (3R)-N-tert-butyloxycarbonyl-3-hydroxymethylpyrrolidine (5.4 g, 26.7 mmol) and anhydrous triethylamine (2.97 g, 29.39 mmol), in $CH_2Cl_2$ (100 ml), at −15° C. The mixture was warmed to room temperature and stirred for 16 h before adding saturated $K_2CO_3$ solution (50 ml) and diluting with $CH_2Cl_2$ (100 ml). The aqueous was separated and extracted further with $CH_2Cl_2$ (2×100 ml). The combined extracts were dried ($Na_2SO_4$) and evaporated to give the title-mesylate (7.5 g, 100%), δ (250 MHz, $CDCl_3$) 1.46 (9H, s, OC(Me)$_3$), 1.62–1.84 (1H, m, CH of $CH_2$), 2.00–2.14 (1H, m, CH of $CH_2$), 2.58–2.72 (1H, m, CH), 3.04 (3H, s, Me), 3.08–3.62 (4H, m, 2 of $CH_2$), 4.11–4.33 (2H, m, $CH_2$OMs).

c) (3S)-N-tert-Butyloxycarbonyl-3-N-(benzyl) aminomethylpyrrolidine

A solution of the preceding mesylate (5.0 g, 17.90 mmol) and benzylamine (9.8 ml, 89.7 mmol) in toluene (25 ml) was heated at reflux for 18 h. The mixture was evaporated under high vacuum and the residue taken up in ethyl acetate (200 ml) and washed with water (×3). The organic layer was dried (MgSO$_4$) and evaporated and the crude product chromatographed on silica gel eluting with $CH_2Cl_2$/MeOH (98:2) to give the desired product (4.9 g, 94%), δ (250 MHz, $CDCl_3$) 1.45 (9H, s, OC(Me)$_3$), 1.52–1.64 (1H, m, CH), 1.92–2.08 (1H, m, CH of $CH_2$), 2.27–2.40 (1H, m, CH of $CH_2$), 2.60–2.68 (2H, m, $CH_2$), 2.93–3.08 (1H, m, CH of $CH_2$), 3.18–3.60 (3H, m, $CH_2$ and CH of $CH_2$), 3.80 (2H, s, NHC$\underline{H}_2$Bn), 7.26–7.36 (5H, m, Ar—H).

d) (3S)-N(H)-3-(N-Benzyl)aminomethyl Pyrrolidine

A solution of the preceding benzylamine (4.9 g, 16.8 mmol) in 90% formic acid (90 ml) was stirred at room temperature for 18.5 h. The reaction was quenched by addition of MeOH and the solvents were removed under vacuum. The residue was dissolved in a minimum volume of $H_2O$, basified with saturated $K_2CO_3$ solution and extracted with n-butanol (3×100 ml). The combined extracts were evaporated in vacuo and the inorganics removed by trituration with $CH_2Cl_2$ and filtration. The filtrate was dried MgSO$_4$) and evaporated to give the title-pyrrolidine (3.24 g, 100%), δ (360 MHz, $CDCl_3$) 1.42–1.60 (1H, m, CH), 1.94–2.03 (1H, m, CH of $CH_2$), 2.24–2.36 (1H, m, CH of $CH_2$), 2.58–2.73 (3H, m, $CH_2$ and CH of $CH_2$), 2.94–3.19 (3H, m, $CH_2$ and CH of $CH_2$), 3.79 (2H, m, NHC$\underline{H}_2$Bn), 7.23–7.35 (5H, m, Ar—H).

2. Intermediate 2: 2-[5-(N-(Methyl)aminosulphonyl-methyl)-1H-indol-3-yl]ethyl Alcohol A. 2-Iodo-4-(N-(methyl)aminosulphonylmethyl)phenyl Aniline a) 1-(N-(Methyl)aminosulphonylmethyl)-4-nitrobenzene A mixture of 4-nitrobenzyl bromide (100.0 g, 0.46 mol), sodium sulphite (84.8 g, 0.67 mol) and water (316 ml) was heated at 90° C. for 5 h. The solution was cooled and the resultant solid filtered and washed with diethyl ether. The product was dried under vacuum at 60° C. (95 g, 86%). Phosphorus pentachloride (78 g, 0.375 mol) was added to sodium 4-nitrobenzylsulphonate (60 g, 0.25 mol) and the mixture heated at 90° C. for 2 h. The mixture was cooled and volatile material removed under vacuum. The residue was dissolved in dichloromethane (500 ml) and water (150 ml). The organic layer was separated, dried over anhydrous sodium sulphate, filtered and evaporated to give 4-nitrobenzyl sulphonyl chloride (48.9 g, 83%) which was pure by $^1$H NMR. Methylamine gas was bubbled through a solution of 4-nitrobenzyl sulphonyl chloride (37.9 g, 0.16 mol), in dichloromethane (325 ml), until uptake had ceased (0.5 h). The resulting solid was filtered, washed with $H_2O$ and dried under vacuum to give the title-sulphonamide (32.5 g, 88%), δ (250 MHz, $D_6$-DMSO) 2.61 (3H, s, Me), 4.55 (2H, s, $CH_2$), 7.06 (1H, s, NH), 7.66 (2H, d, J=8.7Hz, Ar—H), 8.25 (2H, d, J=8.7Hz, Ar—H).

b) 2-Iodo-4-(N-(methyl)aminosulphonylmethyl) phenylaniline

A mixture of the preceding 4-nitro-N-methylbenzenemethane sulphonamide (28.86 g, 0.126 mol), $H_2O$ (100 ml), ethanol (250 ml), 5N HCl (25 ml) and 10% Pd-C (3.0 g) was hydrogenated on a Parr shake apparatus at 50 psi for 4 h. The catalyst was removed by filtration through celite and the solvents removed under vacuum. The residue was dissolved in water (200 ml) and basified with $K_2CO_3$. The precipitated product was filtered off, washed with water and hexane and dried under vacuum at 45° C. to give the desired aniline (21.45 g, 85%) which was pure by $^1$H NMR. To a stirred suspension of the preceding aniline (21.45 g, 0.107 mol) in acetonitrile (250 ml) was added a solution of iodine monochloride (17.41 g, 0.107 mol), in acetonitrile (50 ml), dropwise over 1 h. The mixture was stirred at room temperature for 16 h and then partitioned between ethyl acetate (500 ml) and 20% aqueous sodium thiosulphate (300 ml). The organic layer was separated, washed with $H_2O$ (500 ml) and brine (100 ml) and dried ($Na_2SO_4$). The solvent was removed under vacuum and the crude product chromatographed on silica gel eluting with ethyl acetate/hexane (1:1) to give the title-iodoaniline (9.0 g, 26%), δ (250 MHz, $D_6$-DMSO) 2.51 (3H, d, J=7.4Hz, Me), 4.11 (2H, s, $CH_2$), 5.29 (2H, s, $NH_2$), 6.72 (1H, d, J=8.3Hz, Ar—H), 6.81 (1H, q, J=7.4Hz, NH), 7.06 (1H, dd, J=2.0 and 8.3Hz, Ar—H), 7.53 (1H, d, J=2.0 Hz, Ar—H).

B. 1,4-bis-Triethylsilyl-3-butyn-1-ol n-Butyl lithium (776 ml of a 2.5M solution in hexane, 1.94 mol) was added over a 2 h period to a stirred solution of 3-butyn-1-ol (68 g, 0.97 mol), in anhydrous THF (1.16 l), at −30° C. The mixture was stirred at −30° C. for 1 h (dianion precipitates out) and triethylsilyl chloride (300 g, 1.99 mol) was then added dropwise, ensuring that the temperature remained below −20° C. The solution was stirred at −10° C. for 1 h and then at room temperature for 1 h. Hexane (1.36 l) and $Na_2CO_3$ solution (7.0 g in 700 ml of $H_2O$) were added to the reaction mixture, at −10° C., and the layers separated. The aqueous layer was extracted with hexane and the combined extracts were washed with water, dried ($Na_2SO_4$) and evaporated to give the title-bis triethylsilyl butynol (289 g, 100%), δ (250 MHz, $CDCl_3$) 0.80–0.94 (12H, m, 6 of $SiCH_2CH_3$), 1.22–1.32 (18H, m, 6 of $SiCH_2CH_3$), 2.76 (2H, t, J=7.3Hz, $CH_2$), 4.00 (2H, t, J=7.3Hz, $CH_2$).

C. 2-[5-(N-(Methyl)aminosulphonylmethyl)-1H-indol-3-yl]ethyl Alcohol

A mixture of 2-iodo-4-(N-(methyl) aminosulphonylmethyl)phenyl aniline (10 g, 30.7 mmol), 1,4-bis-triethylsilyl-3-butyn-1-ol (10.97 g, 36.8 mmol) sodium carbonate (16.26 g, 153.4 mmol) and anhydrous DMF (500 ml) was degassed with $N_2$ for 0.5 h. $Pd(OAc)_2$ (0.7 g, 3.1 mmol) was added and the mixture heated at 100° C. for 6 h. The DMF was removed under vacuum and the residue partitioned between EtOAc (250 ml) and water (250 ml). The solutions were passed through celite to remove insolubles and the aqueous layer separated and extracted further with ethyl acetate (4×200 ml). The combined organics were dried ($Na_2SO_4$) and evaporated. The residue was dissolved in methanol (100 ml) and 5N hydrochloric acid (30 ml) was added. The mixture was stirred at room temperature for 2 h and the solvent then removed under vacuum and the residue neutralised with saturated $K_2CO_3$ solution. The aqueous was extracted with EtOAc (200 ml) and n-butanol (2×200 ml) and the combined extracts evaporated under vacuum The residue was chromatographed on silica gel eluting with $CH_2Cl_2$/MeOH/$NH_3$ (60:8:1) to give the title-indole (5.39 g, 66%), mp 114–116° C., δ (250 MHz, $D_6$-DMSO) 2.54 (3H, d, J=4.8Hz, MeNH), 2.83 (2H, t, J=7.5Hz, $CH_2$), 3.60–3.69 (2H, m, $CH_2$—OH), 4.34 (2H, s, $CH_2$), 4.65 (1H, t, J=5.4Hz, OH), 6.78 (1H, q, J=4.8Hz, MeNH), 7.06 (1H, dd, J=2.2 and 8.3Hz, Ar—H), 7.16 (1H, d, J=2.2Hz, Ar—H), 7.31 (1H, d, J=8.3Hz, Ar—H), 7.51 (1H, s, Ar—H), 10.86 (1H, s, NH).

3. (3S)-3-(N-Benzyl)aminomethyl-1-[2-(5-(N-(methyl) aminosulphonylmethyl)-1H-indol-3-yl)ethyl]pyrrolidine 2.1 Hydrogen Oxalate 0.7 Diethyl Etherate Methane sulphonyl chloride (0.32 g, 2.80 mmol) was added to a stirred solution of 2-[5-(N-(methyl) aminosulphonylmethyl)-1H-indol-3-yl]ethyl alcohol (0.50 g, 1.87 mmol) and triethylamine (0.38 g, 3.73 mmol), in dichloromethane (15 ml) and acetonitrile (15 ml), at 0° C. The mixture was warmed to room temperature and stirred for 3 h. Ethyl acetate (70 ml) was added to the mixture and the solution washed with water (40 ml) and brine (40 ml). The organic was dried ($MgSO_4$) and evaporated. The residue was dissolved in anhydrous acetonitrile (7 ml) and IPA (55 ml) and $Na_2CO_3$ (0.26 g, 2.5 mmol) and Intermediate 1 (0.47 g, 2.5 mmol) were added. The mixture was heated at reflux for 16 h and then cooled to room temperature and the insolubles filtered off. The solvent was removed under vacuum and the residue chromatographed on silica gel eluting with $CH_2Cl_2$/MeOH/$NH_3$ (60:8:1) and then again on alumina (Activity III) eluting with $CH_2Cl_2$/MeOH (98:2) to give the title-ethylpyrrolidine (58 mg, 8%). The 2.1 hydrogen oxalate 0.7 diethyl etherate salt was prepared, mp 224–226° C., (Found: C, 54.74, H, 5.99, N, 7.95. $C_{24}H_{32}N_4SO_2.2.1(C_2H_2O_4).0.7(Et_2O)$ requires C, 54.63, H. 6.39, N, 8.22%), m/e 441 (M+1)$^+$, δ (360 MHz, $D_6$-DMSO) 1.70–1.84 (1H, m, CH), 2.12–2.26 (1H, m, CH), 2.50 (3H, s, MeNH), 2.66–2.80 (1H, m, CH), 2.94–3.56 (10H, m, 5 of $CH_2$), 4.13 (2H, s, $CH_2$), 4.34 (2H, s, $CH_2$), 6.81 (1H, br s, NH), 7.12 (1H, d, J=8.4Hz, Ar—H), 7.26 (1H, s, Ar—H), 7.36 (1H, d J=8.4Hz, Ar—H), 7.40–7.52 (5H, m, Ar—H), 7.56 (1H, s, Ar—H), 11.04 (1H, s, NH).

EXAMPLE 2

(3S)-3-(N-Benzyl)aminomethyl-1-[2-(5-(aminosulphonylmethyl)-1H-indol-3-yl)ethyl] pyrrolidine 2.0 Hydrogen Oxalate 0.75 Hydrate 1. Intermediate 3: 2-[5-(Aminosulphonylmethyl)-1H-indol-3-yl]ethyl Alcohol Prepared from 4-nitrobenzene methane sulphonamide using the procedures described for Intermediate 2, mp 173–175° C., δ, ($D_6$-DMSO) 2.83 (2H, t, J=7.4Hz, $CH_2$), 3.61–3.69 (2H, m, $CH_2$), 4.29 (2H, s, $\underline{CH_2}SO_2$), 4.64 (1H, t, J=5.3Hz, OH), 6.70 (2H, s, NH2), 7.06 (1H, dd, J=1.6 and 8.4Hz, Ar—H), 7.16 (1H, d, J=1.6Hz, Ar—H), 7.31 (1H, d, J=8.4Hz, Ar—H), 7.50 (1H, s, Ar—H), 10.84 (1H, s, NH).

2. (3S)-3-(N-Benzyl)aminomethyl-1-[2-(5-(aminosulphonylmethyl)-1H-indol-3-yl)ethyl]pyrrolidine 2.0 Hydrogen Oxalate 0.75 Hydrate Prepared from Intermediates 1 and 3 using the procedure described for Example 1. The 2.0 hydrogen oxalate 0.75 hydrate salt was prepared, mp 203–205° C., (Found: C, 52.52, H, 5.90, N, 8.72; $C_{23}H_{30}N_4SO_2.2(C_2H_2O_4).0.75H_2O$ requires C, 52.29, H. 5.77, N, 9.03%) m/e 426 (M+1)$^+$, δ (360 MHz, $D_6$-DMSO) 1.68–1.82 (1H, m, CH), 2.12–2.24 (1H, m, CH), 2.68–2.78 (1H, m, CH), 2.98–3.54 (1OH, m, 5 of $CH_2$), 4.11 (2H, s, $CH_2$), 4.31 (2H, s, $CH_2$), 6.72 (2H, s, $NH_2$), 7.11 (1H, d, J=1.5 and 8.4Hz, Ar—H), 7.25 (1H, d, J=1.5Hz, Ar—H), 7.35 (1H, d, J=8.4Hz, Ar—H), 7.40–7.52 (5H, m, Ar—H), 7.55 (1H, s, Ar—H), 11.02 (1H, s, NH).

EXAMPLE 3

(3S)-3-(N-Benzyl)aminomethyl-(S)-1-[2-(5-(2-oxo-1 3-oxazolidin-4-ylmethyl)-1H-indol-3-yl)ethyl] pyrrolidine. 3.0 Hydrogen Oxalate 1. Intermediate 4: (S)-2-[5-(2-oxo-1,3-oxazolidin-4-ylmethyl)-1H-indol-3-yl]ethyl Alcohol a) (S)-4-(4-Aminobenzyl)-1,3-oxazolidin-2-one Prepared as described in WO 91/18897.

(b) (S)-4-(3-Iodo-4-aminobenzyl)-1,3-oxazolidin-2-one

A solution of iodine monochloride (4.84 g, 29.8 mmol) in methanol (35 ml) was added dropwise to a stirred mixture of (S)-4-(4-aminobenzyl)-1,3-oxazolidin-2-one (5.2 g, 27.0 mmol) and calcium carbonate (5.42 g, 54.2 mmol) in methanol (115 ml), at −40° C. The reaction was allowed to warm to room temperature and stir for 16 h. The solvent was removed under reduced pressure, the residue taken up into ethyl acetate (300 ml) and washed with 20% aqueous sodium thiosulphate (100 ml). The organic layer was separated, washed with water (50 ml) and brine (50 ml), dried ($Na_2SO_4$) and evaporated. The crude product was chromatographed on silica gel eluting with $CH_2Cl_2$/MeOH/ 98:2 to give the title-iodoaniline (3.88, 45%), δ (250 MHz, D$_6$-DMSO) 2.55–2.60 (2H, m, CH$_2$), 3.90–3.99 (2H, m, CH$_2$O), 4.19–4.28 (1H, m, CHNH), 5.09 (2H, s, NH$_2$), 6.69 (1H, d, J=8.2Hz, Ar—H), 6.95 (1H, dd, J=1.9 and 8.2Hz, Ar—H), 7.44 (1H, d, J=1.9Hz, Ar—H). 7.74 (1H, s, NH).

c) (S)-2-[5-(2-oxo-1,3-oxazolidin-4-ylmethyl)-1 H-indol-3-yl]ethyl Alcohol

Prepared from (S)-4-(3-iodo-4-aminobenzyl)-1,3-oxazolidin-2-one and 1,4-bis-triethylsilyl-3-butyn-1-ol as described for Intermediate 2, δ (360 MHz, D$_6$-DMSO) 2.74–2.91 (4H, m, 2 of CH$_2$), 3.64 (2H, t, J=7.3Hz, CH$_2$), 4.00–4.08 (2H, m, CH$_2$), 4.20–4.26 (1H, m, CH), 6.92 (1H, dd, J=1.4 and 8.2Hz. Ar—H), 7.10 (1H, s, Ar—H), 7.25 (1H, d, J=8.2Hz, Ar—H), 7.36(1H, s, Ar—H), 7.75 (1H, s, NH), 10.69 (1H, s. NH).

2. (3S)-3-(N-Benzyl)aminomethyl-(S)-1-[2-(5-(2-oxo-1,3-oxazolidin-4-ylmethyl)-1H-indol-3-yl)ethyl]pyrrolidine. 3.0 Hydrogen Oxalate Prepared from Intermediates 1 and 4 using the procedure described for Example 1. The 3.0 hydrogen oxalate salt was prepared, mp 196–197° C., (Found: C, 54.46, H, 5.12, N, 7.63. C$_{26}$H$_{32}$N$_4$O$_2$. 3.0 (C$_2$H$_2$O$_4$) requires C, 54.70, H, 5.45, N, 7.97%), m/e 433 (M+1)$^+$, δ (360 MHz, D$_6$-DMSO) 1.72–1.86 (1H, m, CH), 2.14–2.27 (1H, m, CH), 2.68–3.64 (13H, m, 6 of CH$_2$ and CH), 3.99–4.24 (2H, m, CH$_2$), 4.16 (2H, s, CH$_2$), 4.20–4.26 (1H, m, CH), 6.98 (1H, d, J=8.6Hz, Ar—H), 7.20 (1H, s, Ar—H), 7.29 (1H, d, J=8.6Hz, Ar—H), 7.38–7.54 (6H, m, Ar—H), 7.80 (1H, s, NH), 10.91 (1H, s, NH).

EXAMPLE 4

(3S)-3-[N-(R)-α-(Hydroxymethyl)benzyl] aminomethyl-(S)-1-[2-(5-(2-oxo-1,3-oxazolidin-4-ylmethyl)-1H-indol-3-yl)ethyl]pyrrolidine. 2.2 Hydrogen Oxalate 0.5 Hemihydrate 1. Intermediate 5: (3S)-N(H)-3-[(R)-α-(Hydroxymethyl) benzyl]aminomethylpyrrolidine a) (3S)-N-tert-Butyloxycarbonyl-3-[(R)-α (hydroxymethyl)benzyl]aminomethylpyrrolidine A solution of (R)-(−)-phenylglycinol (2.20 g, 16.1 mmol) and (3R)-N-tert-butyloxycarbonyl-3-methylsulphonyloxymethylpyrrolidine (Intermediate 1 part b; 1.0 g, 3.58 mmol), in toluene (20 ml), was heated at 150° C. for 6 h in a sealed pressure tube (Aldrich). The solvent was then removed under vacuum and the residue taken up into ethyl acetate (200 ml) and washed with water (×4). The organic was dried (MgSO$_4$) and evaporated and the crude product chromatographed on silica gel eluting with CH$_2$Cl$_2$/MeOH (97:3) to give the title-α-(hydroxymethyl) benzylaminomethylpyrrolidine (1.0 g, 87%), δ (360 MHz,CDCl$_3$) 1.45 (9H, s, OC(Me)$_3$), 1.52–2.60 (5H, m, CH$_2$ and CH), 2.90–3.76 (7H, m, 3 of CH$_2$ and CH), 7.25–7.39 (5H, m, Ar—H).

b) (3S)-N(H)-3-[(R)-α-(Hydroxymethyl)benzyl] aminomethylpyrrolidine

Prepared from the preceding N-Boc pyrrolidine using the procedure described for Intermediate 1 part d, δ (250 MHz, CDCl$_3$) 1.25–1.45 (1H, m, CH of CH$_2$), 1.83–1.97 (1H, m, CH of CH$_2$), 2.14–2.61 (4H, m, 2 of CH$_2$), 2.80–3.09 (3H, m, CH$_2$ and CH), 3.46–3.76 (3H, m, CH$_2$ and CH), 7.25–7.38 (5H, m, Ar—H).

2. (3S)-3-[N-(R)-α-(Hydroxymethyl)benzyl]aminomethyl-(S)-1-[2-(5-(2-oxo-1,3-oxazolidin-4-ylmethyl)-1H-indol-3-yl)ethyl]pyrrolidine 2.2 Hydrogen Oxalate 0.5 Hemihydrate Prepared from Intermediates 4 and 5 using the procedure described for Example 1. The 2.2 hydrogen oxalate 0.5 hemihydrate salt was prepared, mp 115–117° C., (Found: C, 56.37, H, 6.19, N, 8.67. C$_{27}$H$_{34}$N$_4$O$_3$. 2.2 (C$_2$H$_2$O$_4$). 0.5H$_2$O requires C, 56.32, H, 5.93, N, 8.37%), m/e 463 (M+1)$^+$, δ (360 MHz, D$_6$-DMSO) 1.60–1.76 (1H, m, CH of CH$_2$), 2.08–2.22 (1H, m, CH of CH$_2$), 2.46–4.68 (19H, m, 8 of CH$_2$ and 3 of CH), 6.98 (1H, d, J=8.4Hz, Ar—H), 7.20 (1H, s, Ar—H), 7.29 (1H, d, J=8.4Hz, Ar—H), 7.32–7.46 (6H, m, Ar—H), 7.80 (1H, s, NH), 10.90 (1H, s, NH).

EXAMPLE 5

(3S)-3-[N-(S)-α-Methylbenzyl]aminomethyl-(S)-1-[2-(5-(2-oxo-1,3-oxazolidin-4-ylmethyl)-1H-indol-3-yl)ethyl]pyrrolidine. 2.4 Hydrogen Oxalate Prepared from (S)-2-[5-(2-oxo-1,3-oxazolidin-4-ylmethyl)-1H-indol-3-yl]ethyl alcohol and (3S)-N(H)-3-(N-(S)-α-methylbenzyl)aminomethyl pyrrolidine using the procedures described for Example 4. The 2.4 hydrogen oxalate salt was prepared, mp 115–117° C., (Found: C, 57.77, H, 5.93, N, 8.77. C$_{27}$H$_{34}$N$_4$O$_2$ requires C, 57.64, H, 5.90, N, 8.45%), m/e 447 (M+1)$^+$. δ (360 MHz, D$_6$-DMSO) 1.51 (2H, d, J=6.7Hz, Me), 1.60–1.72 (1H, m, CH of CH$_2$), 2.10–2.20 (1H, m, CH of CH$_2$), 2.48–4.60 (17H, m, 7-CH$_2$ and 3 of CH), 6.97 (1H, d, J=8.3Hz, Ar—H), 7.19 (1H, s, Ar—H), 7.28 (1H, d, J=8.3Hz, Ar—H), 7.34–7.52 (6H, Ar—H and NH), 7.80 (1H, s, Ar—H), 10.89 (1H, s, NH).

EXAMPLE 6

4-[N-(R)-α-(Hydroxymethyl)benzyl]amino-(S)-1-[3-(5-(2-oxo-1,3-oxazolidin-4-ylmethyl)-1H-indol-3-yl) propyl]piperidine. 2.15 Hydrogen Oxalate 1. (S)-3-[5-(2-oxo-1,3-oxazolidin-4-yl)methyl)-1H-indol-3-yl]propan-1-ol The title compound was prepared in 61% yield from (S)-4-(3-iodo-4-aminobenzyl)-1,3-oxazolidin-2-one and 1,5-bis-triethylsilyl-4-pentyn-1-ol as described for Intermediate 2. δ (360 MHz, DMSO-d$_6$) 1.78 (2H, qn, J=7.9Hz), 2.69 (2H, t, J=7.4Hz), 2.77 (1H, dd, J=13.5 and 7.1 Hz), 2.89 (1H, dd, J=13.5 and 4.6Hz), 3.46 (2H, q, J=5.3Hz), 3.98–4.08 (2H, m), 4.18–4.28 (1H,m), 4.42 (1H, t, J=5.1 Hz), 6.92 (1H, dd, J=8.3 and 1.5Hz), 7.06 (1H, d, J=2.1 Hz), 7.24 (1H, d, J=8.3Hz), 7.35 (1H, s). 10.66 (1H, s); m/z (ES) 275 (M$^+$+1).

2. 4-[N-(R)-α-(Hydroxymethyl)benzyl]aminopiperidine

To a stirred solution of N-tert-butyloxycarbonyl-4-piperidinone (2 g, 10 mmol), (R)-(−)-phenylglycinol (1.65 g, 12 mmol), and glacial acetic acid (2.29 ml, 40 mmol) in methanol (200 ml) was added sodium cyanoborohydride (754 mg, 12 mmol). After being stirred at room temperature, under nitrogen, for 16 hours, the mixture was basified with 4N sodium hydroxide and the methanol was removed under vacuum. The residue was diluted with water (35 ml) and the product extracted with diethyl ether (2×200 ml), washed with brine (1×40 ml), dried (Na$_2$SO$_4$) and concentrated. Flash chromatography (silica gel, dichloromethane-methanol-ammonia, 95:5:0.5) of the residue gave 2.91 g (90.9%) of N-tert-butyloxycarbonyl-4-[N-(R)-α-(hydroxymethyl)benzyl]aminopiperidine.

A solution of the above BOC-protected piperidine (2.9 g) in trifluoroacetic acid (40 ml) and dichloromethane (50 ml) was allowed to stand at room temperature for 16 hours. Solvents were removed under vacuum and the residue was azeotroped with toluene-ethanol (5:1, 150 ml). The residue was dissolved in 4N sodium hydroxide, extracted with dichloromethane (3×150 ml) and the combined organic solutions were washed with brine (1×50 ml), then dried (Na$_2$SO$_4$) and concentrated. Crystallisation from ethyl acetate-hexane (1:10, 200 ml) afforded the title compound as white crystals (1.4 g, 70.4%): δ (360 MHz, DMSO-d$_6$)

0.96–1.12 (2H, m), 1.52 (1H, d, J=12.0 Hz), 1.78–2.06 (2H, br s and d, J=12.6Hz) 2.17–2.32 (3H, m), 2.76–2.90 (2H, m), 3.26 (1H, t, J=8.5Hz), 3.40 (1H, dd, J=10.5 and 4.5Hz), 3.83 (1H, dd, J=8.5 and 4.5Hz), 4.82 (1H, br s), 7.27–7.37 (5H, m); m/z (ES) 221 (M$^+$+1).

3. 4-[N-(R)-α-(Hydroxymethyl)benzyl]amino-(S)-1-[3-(5-(2-oxo-1,3-oxazolidin-4-ylmethyl)-1H-indol-3-yl)propyl] piperidine. 2.15 Hydrogen Oxalate The title compound free base was prepared from the products of steps 1 and 2 using a similar method to that described for Example 1. The oxalate salt was prepared from ethanol: mp 156–163° C.; (Found: C. 57.85; H, 5.97; N, 8.63. $C_{28}H_{36}N_4O_3 \times 2.15$ $C_2H_2O_4$ requires: C, 57.89. H, 6.06: N, 8.36%); m/z (ES) 477 (M$^+$+1); δ (360 MHz, DMSO-d$_6$) 1.66–1.85 (2H, m), 1.92–2.18 (4H, m), 2.62–3.00 (9H, m), 3.30–3.42 (2H, m), 3.58–3.70 (2H, m), 3.98–4.10 (2H, m), 4.14–4.28 (2H, m), 6.95 (1H, d, J=8.3Hz), 7.11 (1H, s), 7.26 (1H, d, J=8.3Hz), 7.30–7.52 (4H, m), 7.79 (1H, s), 10.77 (1H, s).

EXAMPLE 7

(3S)-3-(N-Benzyl-N-methyl)aminomethyl-(S)-1-[2-(5-(3-methyl-2-oxo-1,3-oxazolidin-4-ylmethyl)-1H-indol-3-yl)ethyl]pyrrolidine. Sesquioxalate. Hemihydrate 1. Intermediate 6: (S)-2-[5-(3-Methyl-2-oxo-1,3-oxazolidin-4-ylmethyl)-1H-indol-3-yl]ethyl Alcohol a) (S)-3-Methyl-4-(4-aminobenzyl)-1,3-oxazolidin-2-one Prepared as described in WO 91/18897.

b) (S)-2-[5-(3-Methyl-2-oxo-1,3-oxazolidin-4-ylmethyl)-1H-indol-3-yl]ethyl Alcohol Prepared from (S)-3-methyl-4-(3-iodo-4-aminobenzyl)-1,3-oxazolidin-2-one and 1,4-bis-triethylsilyl-3-butyn-1-ol as described for Intermediate 2, δ (360 MHz, D$_6$-DMSO) 2.72–2.84 (6H, m, CH of CH$_2$, CH$_2$ and N—Me), 3.13 (1H, dd, J=3.8 and 13.5Hz, CH of CH$_2$), 3.61–3.67 (2H, m, CH$_2$), 3.94–4.02 (2H, m, CH$_2$), 4.11–4.17 (1H, m, CH), 4.58 (1H, t, J=5.3Hz, OH), 6.93 (1H, dd, J=1.5 and 8.3Hz, Ar—H), 7.10 (1H, d. J=1.5Hz, Ar—H), 7.26 (1H, d, J=8.3Hz, Ar—H), 7.38 (1H, s, Ar—H), 10.72 (1H, s, NH).

2. Intermediate 7: (3S)-N(H)-3-(N-Benzyl-N-methyl)-aminomethylpyrrolidine

Prepared from (3R)-N-tert-butyloxycarbonyl-3-hydroxymethylpyrrolidine and N-methylbenzylamine using the procedures described for Intermediate 1, δ (250 MHz, D$_6$-DMSO) 1.41–1.55 (1H, m, CH of CH$_2$), 1.89–2.02 (1H, m, CH of CH$_2$), 2.11 (3H, s, Me), 2.31 (2H, d, J=7.5Hz, CH$_2$NMe), 2.38–2.52 (1H, m, CH), 2.73 (1H, dd, J=6.9 and 11.3Hz, CH of CH$_2$), 2.95–3.23 (5H, m, 2 of CH$_2$ and CH of CH$_2$), 3.46 (2H, ABq, J=13.4Hz, NCH$_2$—Ar), 7.19–7.36 (5H, m, Ar—H).

3. (3S)-3-(N-Benzyl-N-methyl)aminomethyl-(S)-1-[2-(5-(3-methyl-2-oxo-1,3-oxazolidin-4-ylmethyl)-1H-indol-3-yl)ethyl]pyrrolidine. Sesquioxalate. Hemihydrate Prepared from Intermediates 6 and 7 using the procedure described for Example 1. The sesquioxalate hemihydrate salt was prepared, mp 102–104° C., (Found: C, 61.73; H, 7.02; N, 9.02. $C_{28}H_{36}N_4O_2 \cdot 1.5(C_2H_2O_4) \cdot 0.5H_2O$) requires C, 61.58; H, 6.67; N, 9.26%), m/e 461 (M+1)$^+$, δ (360 MHz, D$_6$-DMSO) 1.60–1.72 (1H, m, CH of CH$_2$), 2.08–2.20 (1H, m, CH of CH$_2$), 2.17 (3H, s, N—Me), 2.44–4.16 (18H, m, 2 of CH and 8 of CH$_2$), 2.83 (3H, s, N—Me), 7.00 (1H, d, J=8.5Hz, Ar—H), 7.23 (1H, s, Ar—H), 7.24–7.36 (6H, m, Ar—H), 7.44 (1H, s, Ar—H), 10.93 (1H, s, NH).

EXAMPLE 8

(3R)-3-[N-(S)-α-Methylbenzyl-N-methyl] aminomethyl-(S)-1-[2-(5-(2-oxo-1,3-oxazolidin-4-ylmethyl)-1H-indol-3-yl)ethyl]pyrrolidine. 3.0 Hydrogen Oxalate. Hemihydrate a) (3S)-N-tert-Butyloxycarbonyl-3-[N-(S)-α-methylbenzyl]aminomethyl Pyrrolidine Prepared from (3S)-N-tert-butyloxycarbonyl-3-methylsulphonyloxymethylpyrrolidine and (S)-α-methylbenzylamine using the procedure described for Intermediate 5 part a, δ (250 MHz, CDCl$_3$) 1.34 (3H, d, J=6.5Hz, Me), 1.44 (9H, s, OC(Me)$_3$), 1.44–2.60 (5H, m, 2 of CH$_2$ and CH), 2.90–3.54 (4H, m, 2 of CH$_2$), 3.74 (1H, q, J=6.5Hz, CH—Me), 7.18–7.36 (5H, m, Ar—H).

b) (3R)-N-tert-Butyloxycarbonyl-3-[N-(S)-α-methylbenzyl-N-methyl]aminomethylpyrrolidine Glacial acetic acid (0.90 ml, 15.7 mmol) and sodium cyanoborohydride (0.495 g, 7.88 mmol) were added successively to a stirred solution of the preceding α-(methyl) benzylaminomethylpyrrolidine (1.92 g, 6.31 mmol) in anhydrous methanol (150 ml) at 0° C. A solution of formaldehyde (0.623 g, of a 38% w/v solution, 7.88 mmol) in methanol (50 ml) was then added, dropwise. The mixture was stirred at 0° C. for 4.5 h and then at room temperature for 1.25 h. Saturated K$_2$CO$_3$ solution (25 ml) was added and the precipitated inorganics were removed by filtration before removing the solvent in vacuo. The resultant residue was taken up into ethyl acetate and washed with water (×1) and brine (×2), and dried (MgSO$_4$). The crude product remaining, after evaporating the solvent in vacuo, was chromatoraphed on silica gel eluting with CH$_2$Cl$_2$/MeOH (97.5:2.5) to give the title product (2.02 g, 100%), δ (250 MHz, CDCl$_3$) 1.34 (3H, d, J=6.7Hz, Me), 1.44 (9H, s, OC(Me)$_3$), 1.60–1.68 (1H, m, CH of CH$_2$), 1.86–1.98 (1H, m, CH of CH$_2$), 2.19 (3H, s, Me), 2.19–2.42 (3H, m,CH and CH$_2$), 2.80–3.60 (5H, m, CH and 2 of CH$_2$), 7.18–7.32 (5H, m, Ar—H).

c) (3R)-N(H)-3-[N-(S)-α-Methylbenzyl-N-methyl] aminomethyl Pyrrolidine

Prepared from the preceding N-Boc pyrrolidine using the procedure described for Intermediate 1, part d, δ (250 MHz, CDCl$_3$) 1.34 (3H, d, J=6.8Hz, Me), 1.52–1.67 (1H, m, CH of CH$_2$), 1.94–2.08 (1H, m, CH of CH$_2$), 2.17 (3H, s, Me), 2.20–2.52 (3H, m, CH and CH$_2$), 2.72 (1H, dd, J=7.3 and 11.3Hz, CH of CH$_2$), 3.07–3.13 (2H, m, CH$_2$), 3.25 (1H, dd, J=7.3 and 11.3Hz, CH of CH$_2$), 3.57 (1H, q, J=6.8Hz, CH—Me), 7.19–7.34 (5H, m, Ar—H).

d) (3R)-3-[N-(S)-α-Methylbenzyl-N-methyl] aminomethyl-(S)-1-[2-(5-(2-oxo-1,3-oxazolidin-4-ylmethyl)-1H-indol-3-yl)ethyl]pyrrolidine. 3.0 Hydrogen Oxalate. Hemihydrate.

Triethylamine (0.182 ml, 1.3 mmol) was added dropwise to a stirred solution of (S)-2-[5-(2-oxo-1,3-oxazolidin-4-ylmethyl)-1H-indol-3-yl]ethyl alcohol (0.20 g, 0.77 mmol), in anhydrous THF (12 ml). The solution was cooled to 0° C. and methane sulphonyl chloride (0.095 ml, 1.2 mmol) added dropwise. The mixture was warmed to room temperature and stirred for 1 h before filtering and evaporating the filtrate in vacuo. The residue was taken up into dichloromethane (50 ml), washed with water (×2) and dried (MgSO$_4$). The solvent was removed in vacuo to give the desired mesylate (0.305 g) which was used without further purification. Potassium carbonate (0.159 g, 1.15 mmol) and sodium iodide (0.115 g, 0.767 mmol) were added successively to a stirred solution of the preceding mesylate (0.305 g, 0.90 mmol) in anhydrous DMF (20 ml). A solution of (3R)-N-(H)-3-[N-(S)-α-methylbenzyl-N-methyl]aminomethylpyrrolidine (0.286 g, 1.31 mmol), in DMF (5 ml), was then added and the mixture heated at 70° C. for 18 h. The reaction mixture was cooled to room temperature and then poured into ethyl acetate (200 ml) and washed with water (×6). The organic layer was dried (MgSO$_4$) and evaporated in vacuo to give the crude product which was chromatographed on silica gel eluting with CH$_2$CO$_2$/MeOH/NH$_3$ (70:8:1) to give the title-indole (59mg, 14%). The 3.0 hydrogen oxalate hemihydrate salt was prepared, mp 85–90° C. (Hygroscopic), (Found: C, 55.26; H, 5.98; N, 7.60. C$_{28}$H$_{36}$N$_4$O$_2$. 3.0 (C$_2$H$_2$O$_4$). 0.5 H$_2$O requires C, 55.21; H, 5.86; N, 7.57%), m/e461 (M+1)$^+$, δ (360 MHz, D$_6$-DMSO) 1.41 (3H, d, J=6.8Hz, Me), 1.58–1.70 (1H, m, CH of CH$_2$), 2.07–2.20 (1H, m, CH of CH$_2$), 2.27 (3H, s, Me), 2.50–4.24 (17H, m, 3 of CH and 7 of CH$_2$), 6.98 (1H, d, J=8.4Hz, Ar—H), 7.21 (1H, s, Ar—H), 7.26–7.44 (7H, m, Ar—H), 7.80 (1H, s, Ar—H), 10.90 (1H, s, NH).

EXAMPLE 9

(3R)-3-[N-(S)-α-Methylbenzyl-N-methyl]aminomethyl-(S)-1-[2-(5-(3-methyl-2-oxo-1,3-oxazolidin-4-ylmethyl)-1H-indol-3-yl)ethyl]pyrrolidine. 2.5 Hydrogen Oxalate. Monohydrate Prepared from (S)-2-[5-(3-methyl-2-oxo-1,3-oxazolidin-4-ylmethyl)-1H-indol-3-yl]ethyl alcohol (Intermediate 6) and (3R)-N(H)-3-[N-(S)-α-methylbenzyl-N-methyl]aminomethylpyrrolidine using the procedure described for Example 8. The 2.5 hydrogen oxalate monohydrate salt was prepared, low melting point (hygroscopic), (Found: C, 57.01; H, 6.38; N, 7.73. C$_{29}$H$_{39}$N$_4$O$_2$. 2.5(C$_2$H$_2$O$_4$). 1.0H$_2$O requires C, 56.90; H, 6.32; N, 7.81%), m/e 475 (M+1)$^+$, δ (360 MHz, D$_6$-DMSO) 1.42 (3H, d, J=6.8Hz, Me), 1.60–1.74 (1H, m, CH of CH$_2$), 2.06–2.20 (1H, m, CH of CH$_2$), 2.27 (3H, s, Me), 2.40–4.20 (17H, m, 3 of CH and 7 of CH$_2$), 2.84 (3H, s, Me), 7.00 (1H, d, J=8.4Hz, Ar—H), 7.23 (1H, s, Ar—H), 7.32 (1H, d, J=8.4Hz, Ar—H), 7.34–7.40 (5H, m, Ar—H), 7.44 (1H, s, Ar—H), 10.94 (1H, s, NH).

EXAMPLE 10

(3S)-3-[N-(4-Fluorobenzyl)-N-methyl]aminomethyl-(S)-1-[2-(5-(3-methyl-2-oxo-1,3-oxazolidin-4-ylmethyl)-1H-indol-3-yl)ethyl]pyrrolidine. 1.65 Hydrogen Oxalate. 0.6 Hydrate The title-compound was prepared from (S)-2-[5-(3-methyl-2-oxo-1,3-oxazolidin-4-ylmethyl)-1H-indol-3-yl] ethyl alcohol and (3S)-3-[N-(4-fluorobenzyl)-N-methyl] aminomethylpyrrolidine using the procedure described for Example 8. The 1.65 hydrogen oxalate 0.6 hydrate salt was prepared, mp 88–89° C., (Found: C, 58.71; H, 6.56; N, 8.82. C$_{28}$H$_{35}$N$_4$O$_2$F. 1.65(C$_2$H$_2$O$_4$). 0.6H$_2$O requires C, 58.93; H, 6.24; N, 8.78%), m/e 479 (M+1)$^+$, δ (360 MHz, D$_6$-DMSO) 1.56–1.68 (1H, m, CH of CH$_2$), 2.04–2.20 (4H, m, Me and CH of CH$_2$), 2.40–4.18 (18H, m, 2 of CH and 8 of CH$_2$), 2.82 (3H, s, Me), 6.99 (1H, d, J=8.3Hz, Ar—H), 7.12–7.36 (6H, m, Ar—H), 7.43 (1H, s, Ar—H), 10.92 (1H, s, NH).

What is claimed is:
1. A compound of formula I, or a salt or prodrug thereof:

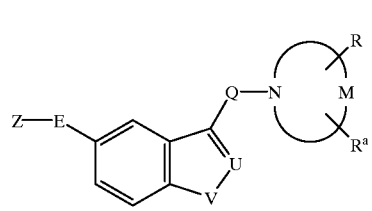

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (a), (b), (c) or (d):

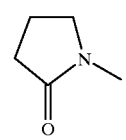

(a)

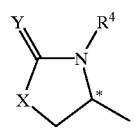

(b)

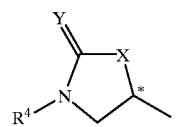

(c)

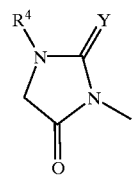

(d)

in which the asterisk * denotes a chiral centre;
X represents oxygen, sulphur, —NH— or methylene;
Y represents oxygen or sulphur;
E represents a chemical bond or a straight or branched alkylene chain containing from 1 to 4 carbon atoms;
Q represents a straight or branched alkylene chain containing from 1 to 4 carbon atoms, optionally substituted in any position by a hydroxy group;
U represents nitrogen or C—R$^2$;
V represents oxygen, sulphur or N—R$^3$;
R$^2$, R$^3$ and R$^4$ independently represent hydrogen or C$_{1-6}$ alkyl;
R$^5$ and R$^6$ independently represent hydrogen, C$_{1-6}$ alkyl, trifluoromethyl, phenyl, methylphenyl, or an optionally substituted aryl(C$_{1-6}$)alkyl or heteroaryl(C$_{1-6}$)alkyl group; or R$^5$ and R$^6$, when linked through a nitrogen atom, together represent the residue of an optionally substituted azetidine, pyrrolidine, piperidine, morpholine or piperazine ring;

M represents the residue of an azetidine, pyrrolidine or piperidine ring;

R represents a group of formula —W—$R^1$;

W represents a chemical bond or a straight or branched alkylene chain containing from 1 to 4 carbon atoms;

$R^1$ represents —$OR^x$, —$SR^x$ or —$NR^xR^y$;

$R^x$ and $R^y$ independently represent hydrogen, hydrocarbon or a heterocyclic group, or $R^x$ and $R^y$ together represent a $C_{2-6}$ alkylene group; and $R^a$ represents hydrogen, hydroxy, hydrocarbon or a heterocyclic group.

2. A compound as claimed in claim 1 wherein Z represents —$SO_2NR^5R^6$ in which $R^5$ and $R^6$ are as defined in claim 1.

3. A compound as claimed in claim 1 wherein Z represents a group of formula (b) as defined in claim 1.

4. A compound as claimed in claim 1 represented by formula IIA, and salts and prodrugs thereof:

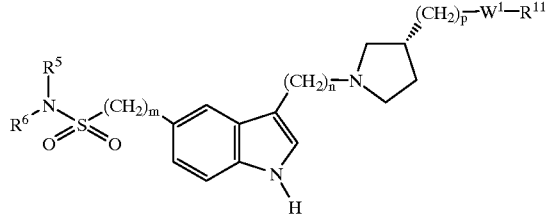

(IIA)

wherein m is zero, 1, 2 or 3;

n is 2, 3 or 4;

p is zero, 1 or 2;

$R^5$ and $R^6$ are as defined in claim 1;

$W^1$ represents oxygen, sulphur or N—$R^{12}$; and $R^{11}$ and $R^{12}$ independently represent hydrogen, $C_{1-6}$ alkyl, aryl, aryl($C_{1-6}$)alkyl, heteroaryl or heteroaryl($C_{1-6}$)alkyl, any of which groups may be optionally substituted.

5. A compound as claimed in claim 1 represented by formula IIB, and salts and prodrugs thereof:

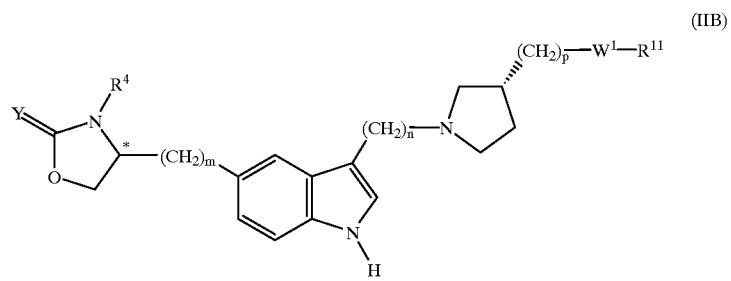

(IIB)

wherein the asterisk * denotes a chiral centre;

$R^4$ and Y are as defined in claim 1; and m is zero, 1, 2 or 3;

n is 2, 3 or 4;

p is zero, 1 or 2;

$R^5$ and $R^6$ are as defined in claim 1;

$W^1$ represents oxygen, sulphur or N—$R^{12}$; and $R^{11}$ represents hydrogen, $C_{1-6}$ alkyl, aryl, aryl($C_{1-6}$)alkyl, heteroaryl or heteroaryl($C_{1-6}$)alkyl, any of which groups may be optionally substituted.

6. A compound as claimed in claim 1 represented by formula IIC, and salts and prodrugs thereof:

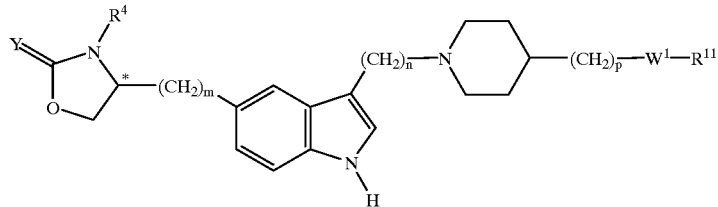

(IIC)

wherein the asterisk * denotes a chiral centre;

$R^4$ and Y are as defined in claim 1; and m is zero, 1, 2 or 3;

n is 2, 3 or 4;

p is zero, 1 or 2;

$R^5$ and $R^6$ are as defined in claim 1;

$W^1$ represents oxygen, sulphur or N—$R^{12}$; and $R^{11}$ represents hydrogen, $C_{1-6}$ alkyl, aryl, aryl($C_{1-6}$)alkyl, heteroaryl or heteroaryl($C_{1-6}$)alkyl, any of which groups may be optionally substituted.

7. A compound selected from:

(3S)-3-(N-benzyl)aminomethyl-1-[2-(5-(N-methyl)-aminosulphonylmethyl)-1H-indol-3-yl)ethyl]pyrrolidine;

(3S)-3-(N-benzyl)aminomethyl-1-[2-(5-(aminosulphonylmethyl)-1H-indol-3-yl)ethyl]pyrrolidine;

and salts and prodrugs thereof.

8. A compound selected from:

(3S)-3-(N-benzyl)aminomethyl-(S)-1-[2-(5-(2-oxo-1,3-oxazolidin-4-ylmethyl)-1H-indol-3-yl)ethyl]pyrrolidine;

(3S)-3-[N-(R)-α-(hydroxymethyl)benzyl]aminomethyl-(S)-1-[2-(5-(2-oxo-1,3-oxazolidin-4-ylmethyl)-1H-indol-3-yl)ethyl]pyrrolidine;

(3S)-3-[N-(S)-α-methylbenzyl]aminomethyl-(S)-1-[2-(5-(2-oxo-1,3-oxazolidin-4-ylmethyl)-1H-indol-3-yl)ethyl]pyrrolidine;

4-[N-(R)-α-(hydroxymethyl)benzyl]amino-(S)-1-[3-(5-(2-oxo-1,3-oxazolidin-4-ylmethyl)-1H-indol-3-yl)propyl]piperidine;

and salts and prodrugs thereof.

9. A compound selected from:

(3S)-3-(N-benzyl-N-methyl)aminomethyl-(S)-1-[2-(5-(3-methyl-2-oxo-1,3-oxazolidin-4-ylmethyl)-1H-indol-3-yl)ethyl]pyrrolidine;

(3R)-3-[N-(S)-α-methylbenzyl-N-methyl]aminomethyl-(S)-1-[2-(5-(2-oxo-1,3-oxazolidin-4-ylmethyl)-1H-indol-3-yl)ethyl]pyrrolidine;

(3R)-3-[N-(S)-α-methylbenzyl-N-methyl]aminomethyl-(S)-1-[2-(5-(3-methyl-2-oxo-1,3-oxazolidin-4-ylmethyl)-1H-indol-3-yl)ethyl]pyrrolidine;

(3S)-3-[N-(4-fluorobenzyl)-N-methyl]aminomethyl-(S)-1-[2-(5-(3-methyl-2-oxo-1,3-oxazolidin-4-ylmethyl)-1H-indol-3-yl)ethyl]pyrrolidine;

and salts and prodrugs thereof.

10. A pharmaceutical composition comprising a compound as claimed in claim 1 in association with a pharmaceutically acceptable carrier.

11. A process for the preparation of a compound as claimed in claim 1, which comprises;

(A) reacting a compound of formula III:

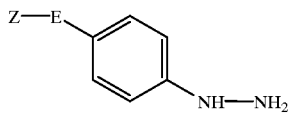

(III)

wherein Z and E are as defined in claim 1; with a compound of formula IV, or a carbonyl-protected form thereof:

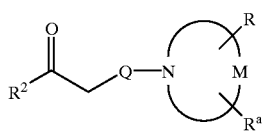

(IV)

wherein $R^2$, Q, M, R and $R^a$ are as defined in claim 1; followed, where required, by N-alkylation by standard methods to introduce the moiety $R^3$; or (B) reacting a compound of formula VII:

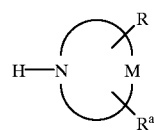

(VII)

wherein M, R and $R^a$ are as defined in claim 1; with a compound of formula VIII:

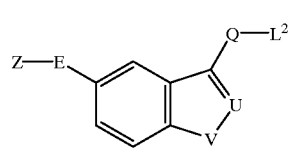

(VIII)

wherein Z, E, Q, U and V are as defined in claim 1, and $L^2$ represents a suitable leaving group; or (C) cyclising a compound of formula X:

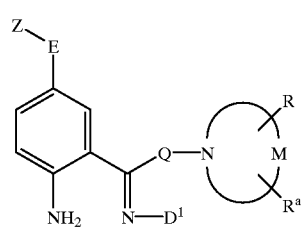

(X)

wherein Z, E, Q, M, R and $R^a$ are as defined in claim 1, and $D^1$ represents a readily displaceable group; followed, where required, by N-alkylation by standard methods to introduce the moiety $R^3$; or (D) cyclising a compound of formula XIII:

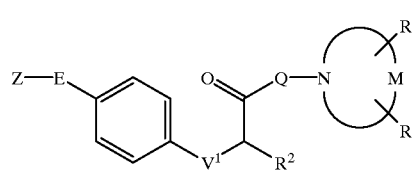

(XIII)

wherein Z, E, Q, $R^2$, M, R and $R^a$ are as defined in claim 1, and $V^1$ represents oxygen or sulphur; and (E) subsequently, where required, converting a compound of formula I initially obtained into a further compound of formula I by conventional methods.

12. A method for the treatment of clinical conditions for which a subtype-selective agonist of 5-HT$_{1D}$ receptors is indicated, which method comprises administering to a patient in need of such treatment an effective amount of a compound as claimed in claim 1.

* * * * *